United States Patent [19]

Le Roux

[11] Patent Number: 4,694,253
[45] Date of Patent: Sep. 15, 1987

[54] PROCESS FOR THE MODULATION OF THE SPEED EFFECT OF MOVING PARTS OF A BODY IN A NUCLEAR MAGNETIC RESONANCE DENSITY MEASUREMENT AND PERFORMANCE OF THE PROCESS IN ORDER TO DEDUCE THEREFROM THE SPEED OF THE MOVING PARTS IN QUESTION

[75] Inventor: Patrick Le Roux, Paris, France
[73] Assignee: Thomson-CGR, Paris, France
[21] Appl. No.: 808,049
[22] Filed: Dec. 12, 1985
[30] Foreign Application Priority Data

Aug. 13, 1985 [FR] France ................................ 85 12352

[51] Int. Cl.$^4$ ............................................ G01R 33/20
[52] U.S. Cl. ..................................... 324/309; 128/653
[58] Field of Search ............... 324/306, 307, 309, 312; 128/653

[56] References Cited

U.S. PATENT DOCUMENTS

| | | | |
|---|---|---|---|
| 4,595,879 | 6/1986 | Lent et al. | 324/306 |
| 4,609,872 | 9/1986 | O'Donnell | 324/306 |
| 4,616,180 | 10/1986 | Compton | 324/309 |

FOREIGN PATENT DOCUMENTS

| | | |
|---|---|---|
| 0115642 | 1/1983 | European Pat. Off. |
| 0142343 | 5/1985 | European Pat. Off. |

OTHER PUBLICATIONS

Radiology, vol. 154, No. 2, Feb. 1985, pp. 433–441, Easton, U.S.; P. R. Moran et al.: "Verification and Evaluation of Internal Flow and Motion", *Chapter: Method, pp 434–435.

Physics in Medicine & Biology, vol. 29, No. 7, Jul. 1984, pp. 891–895, The Institute of Physics, Bristol, GB; T. W. Redpath et al.: "A New Method of NMR Flow Imaging".

Medical Physics, vol. 12, No. 1, Jan.–Feb. 1985, pp. 59–64, Am. Assoc. Phys. Med., New York, U.S.; M. O'Donnell: "NMR Blood Flow Imaging Using Multiecho, Phase Contrast Sequences" * Chapter II, Methods; FIGS. 1, 2.

Primary Examiner—Stewart J. Levy
Assistant Examiner—Kevin D. O'Shea
Attorney, Agent, or Firm—Oblon, Fisher, Spivak, McClelland & Maier

[57] ABSTRACT

The present invention relates to a process for modulating the effect of the speed of the moving parts of a body. The machines or processes for measuring the density by nuclear magnetic resonance are too sensitive at the displacement speed of the parts in question. In the invention, the sensitivity of the machines or processes is reduced in such a way that the speed effect can be measured. Prior to the measurement, compensating magnetic field sequences are applied in order to counteract the effect produced by the interfering magnetic field sequences, which are necessary for performing the measurement.

14 Claims, 5 Drawing Figures

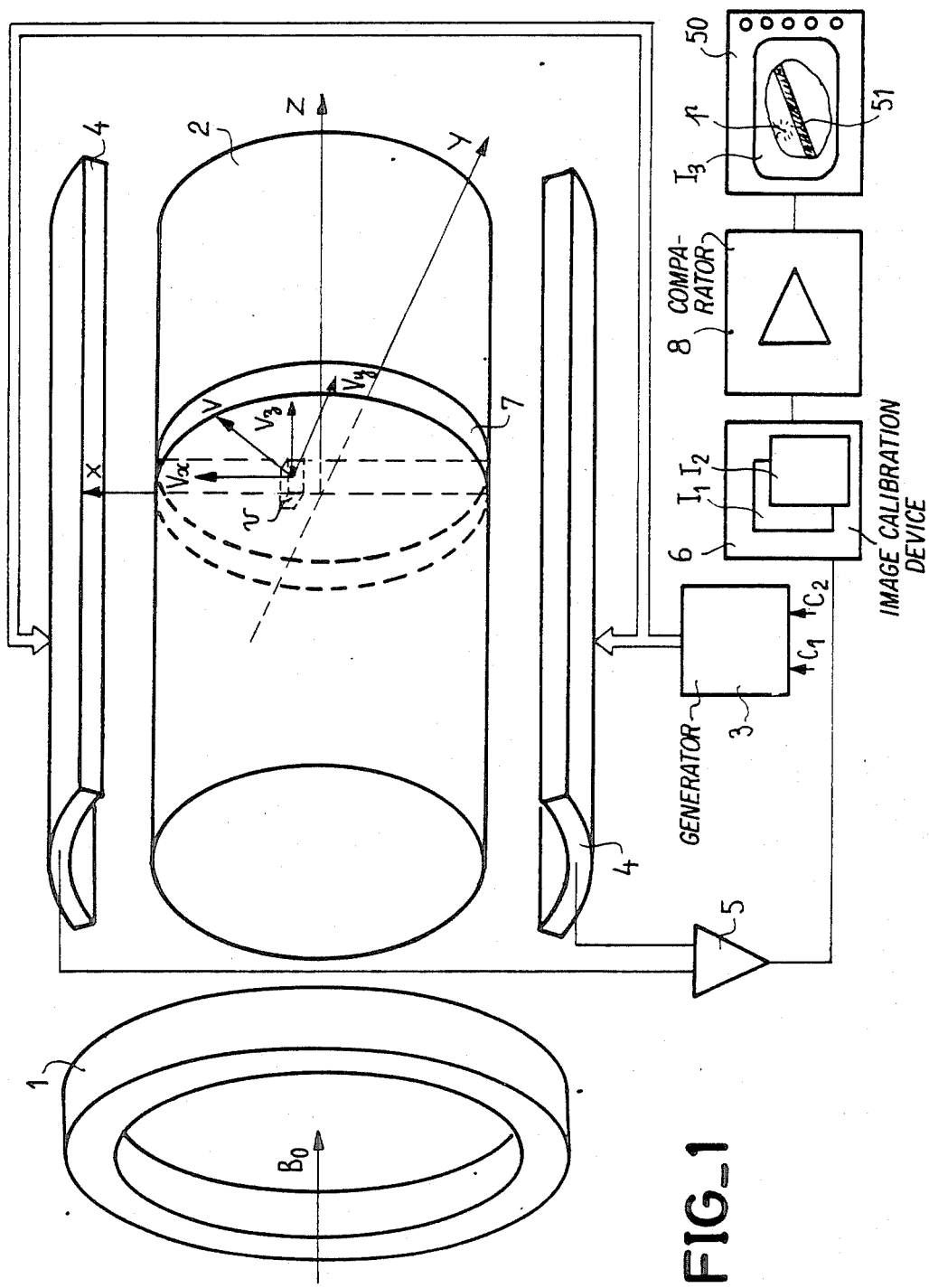
FIG_1

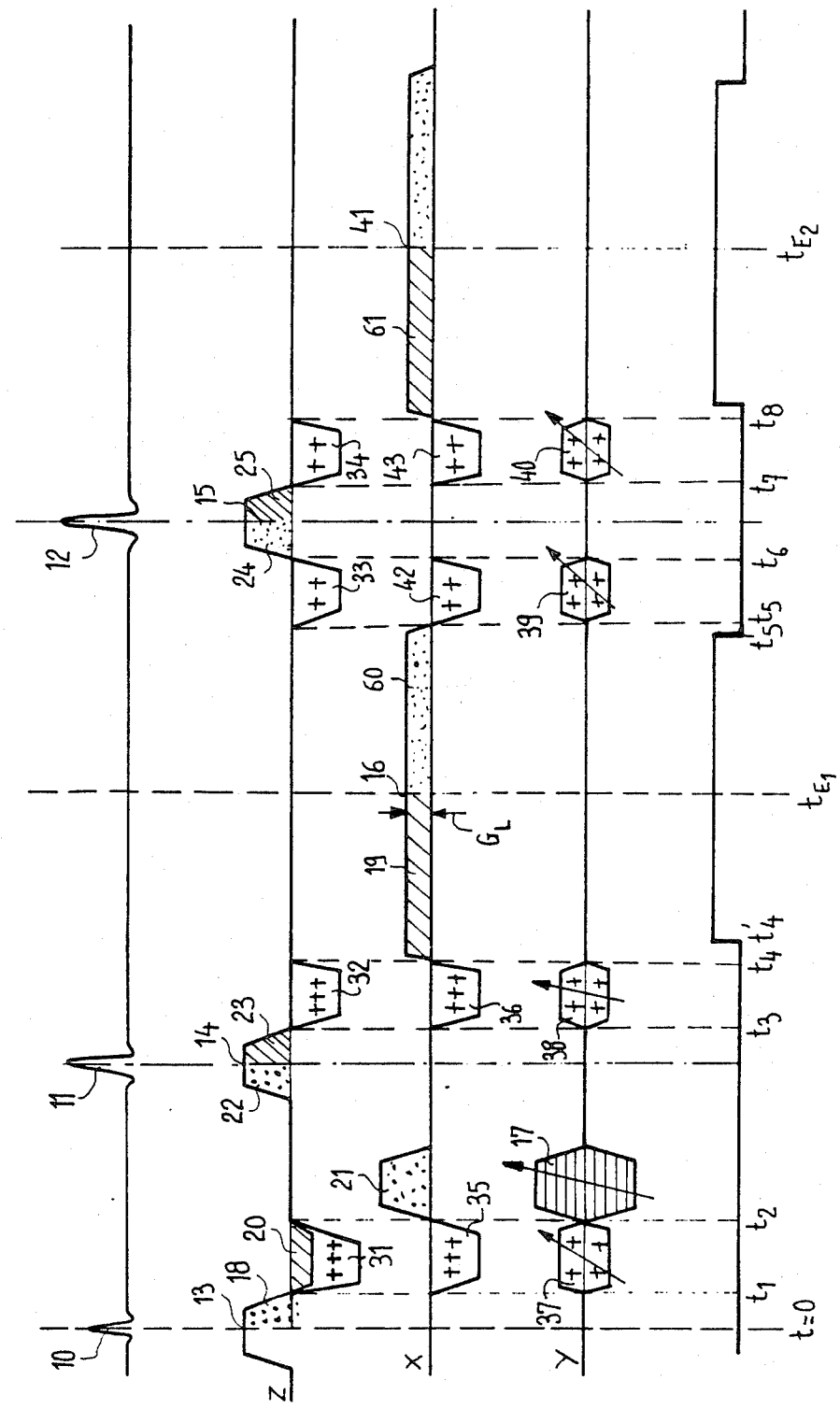

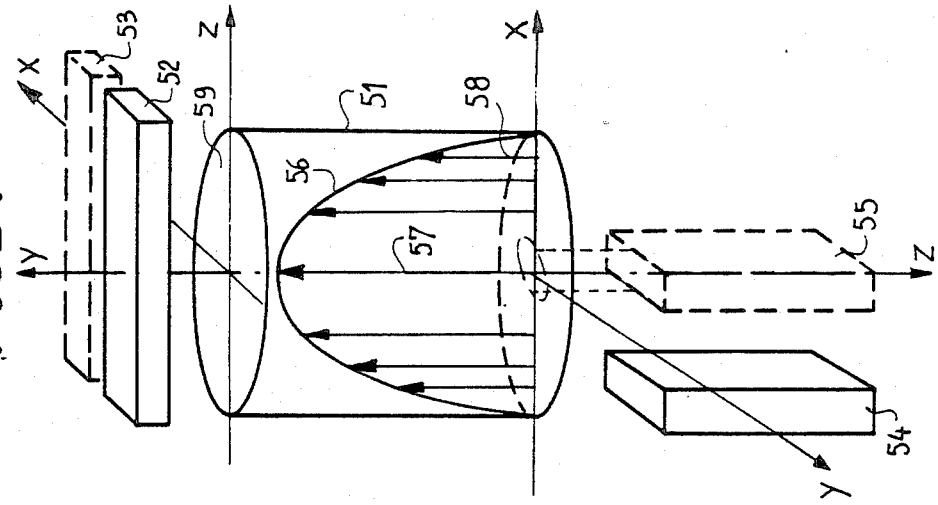
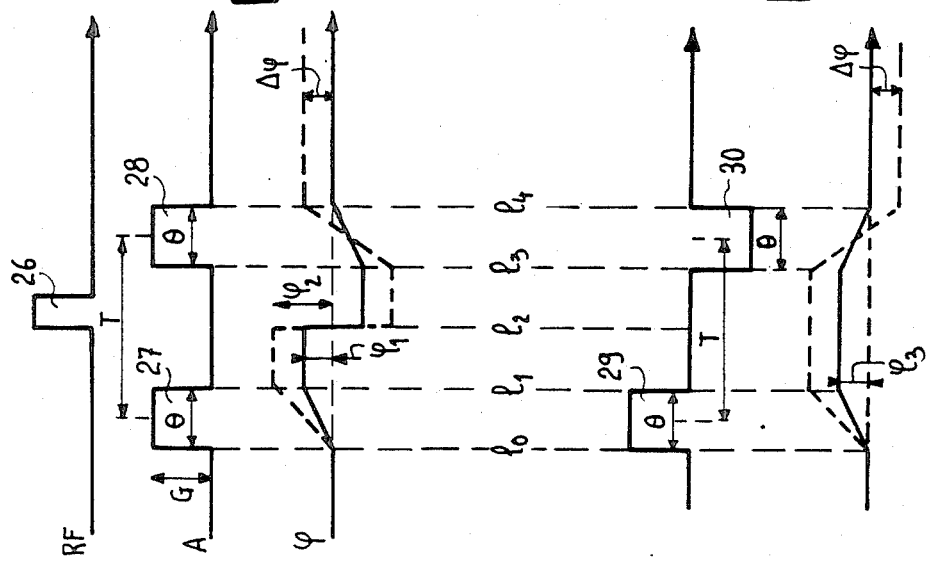

PROCESS FOR THE MODULATION OF THE SPEED EFFECT OF MOVING PARTS OF A BODY IN A NUCLEAR MAGNETIC RESONANCE DENSITY MEASUREMENT AND PERFORMANCE OF THE PROCESS IN ORDER TO DEDUCE THEREFROM THE SPEED OF THE MOVING PARTS IN QUESTION

BACKGROUND OF THE INVENTION

1. FIELD OF THE INVENTION

The present invention relates to a process for modulating the effect of the speed of moving parts of a body in a density measurement by nuclear magnetic resonance (NMR), as well as the performance of the process for deducing therefrom the speed of the moving parts in question. The invention is more particularly used in the medical field, where the bodies examined are human bodies and where the moving parts are cells of the blood circulating in the veins and arteries, or moving organs such as the cardiac muscle. In this application, the invention can be more particularly realised with an imaging or image production process in order to give an image representing the distribution of the speeds of the moving parts in a section of the body examined.

Thus, imaging by nuclear magnetic resonance is mainly developed as a medical diagnosis means. It makes it possible to visually display internal tissue structures with a contrast and a resolution level never simultaneously achieved before with other image production processes.

In order to obtain an image by nuclear magnetic resonance of a section of a body with differentiation of the tissue characteristics thereof, use is made of the property of certain particles, such as protons, of orienting their magnetic moment whilst acquiring energy when they are placed in a constant main magnetic field $B_O$. A particular zone of a body containing particles then has an overall magnetic moment which can be tilted or flipped in accordance with a given orientation, perpendicular or parallel to field $B_O$, by inducing a resonance by the emission of a radiofrequency magnetic field perpendicular to the main field.

All the particles which then have a magnetic moment rotating at a so-called Larmor precession speed, tend to find again the initial orientation parallel to $B_O$ by emitting a radiofrequency signal at the characteristic resonant frequency of $B_O$ and of the particle. This signal can be detected by a receiving antenna. The duration of the return to equilibrium of the overall magnetic moment of a region in question and the decrease of the signal are dependent on two important factors, the spin-system interaction and the spin-spin interaction of the particles with the surrounding material. These two factors lead to the definition of two relaxation times characteristic of the tissue and respectively called $T_1$ and $T_2$. A considered region of an object consequently emits a signal, whose intensity is dependent on $T_1$, $T_2$, the density of the particles in the region and the time which has elapsed since radiofrequency excitation.

2. DESCRIPTION OF THE PRIOR ART

If the orienting field is perfectly homogeneous, in response, mobile particles in a considered region emit a signal identical to that of the fixed particles of said region. However, if the orienting field is not homogeneous, or, more generally if for various reasons (particularly for carrying out image formation) during or after radiofrequency magnetic excitation, an interfering magnetic field is applied which has an intensity gradient, it is possible to show that the contributions made by the mobile particles in the overall signal emitted are affected by a phase component dependent on the speed thereof. This can be easily understood. The resonant signal emitted vibrates at a frequency $f_O$, which is dependent on the intensity of the orienting magnetic field $B_O$ and a gyromagnetic ratio characteristic of the medium in question $\gamma$. All variations in the intensity of the field $B_O$ consequently lead to a corresponding variation of the resonant frequency. Consequently a fixed particle which, following radiofrequency excitation, is exposed firstly to the field $B_O$ resonates at a frequency $f_O$ and then secondly is exposed to a stronger field $B_O + \Delta B_O$, it resonates at a higher frequency $f_O + \Delta f_O$. Thirdly it is again exposed to field $B_O$ and it again vibrates at frequency $f_O$. During the latter the signal emitted is then phase displaced with respect to its phase initially. This phase displacement is proportional to the amplitude of the interference $\Delta B_O$ and to the duration of said interference. If all the particles of the medium does not have a gradient, this simply means that the overall signal emitted is delayed.

However, the procedure is quite different in the case of particles having a certain speed when the interference has a gradient. During three periods and as a result of the displacement speed thereof during these periods, they occupy regions in space where the orienting and interfering fields differ. They differ respectively as a result of the existence of inhomogeneities or the fact that gradients exist. Therefore the contribution of the mobile particles in the signal is provided with a phase dependent not only on the amplitude of the interference encountered (as for fixed particles), but also the amplitude variation of said interferences along the path which they have taken. This variation, which constitutes the gradient is geographically imposed. Consequently the phase displacement of the signal of the mobile particles is then dependent on their speed, because the higher their speed the more regions in space they occupy. If the displacement speeds, inhomogeneity or field gradients are too large, the phases of the different contributions can be affected at this point and end up by providing opposition. In this case, these contributions are mutually cancelled out and the resulting overall signal is not as strong. In practice this effect is such that it often gives the illusion that there is no matter in a body at the location where the mobile particles circulate.

To reveal the existence of mobile particles and to measure their characteristics, the density and possibly the displacement speed, it is possible to proceed in accordance with a method described by E. L. HAHN in February 1960 in the Journal of GEOPHYSICAL RESEARCH, vol. 65, no. 2, p. 776 ff. The author suggests subjecting the medium in question to a sequence of a particular gradient and coding it. The principle of this coding consists of applying following the flipping of the radio-frequency pulse, a bipolar gradient along the axis of a velocity component which it is wished to recognise. A bipolar gradient is such that its time integral is zero from the time corresponding to the start of the radiofrequency pulse to the time corresponding to the measurement. The magnetic moment of the spin of a stationary particle in this case only undergoes a zero overall phase displacement. Thus, the phase displacement undergone during the application of the first part of the bipolar gradient is compensated by the application of the second part of said gradient. However, a mobile particle with a positive speed along the gradient axis then undergoes during the second part of the pulse, a larger phase displacement in absolute values than during the first part. The reason is that during this second part, it frequents a region in space where, due to the gradient, the interfering magnetic field is stronger. By comparing a measurement made with such a bipolar gradient and a measurement made without it being applied, it is possible to deduce therefrom the speed and number of mobile particles.

Whatever the objectives pursued, simple measurement or measurement with an image and no matter what the procedures adopted, the sensitivity of the speed phenomenon to the interfering magnetic field applied is such that the displacement phenomena can only be revealed when the maximum speeds are below a limit. Particularly in image formation, depending on whether the velocity component to be revealed is parallel or perpendicular to the plane of the imaged section, the sensitivity of NMR machines is at present approximately 1 radian (cm/s) to 0.2 radian (cm/s). This means that a particle moving at 1 cm/second in the plane of the section contributes to the overall signal emitted with a phase displacement of 1 radian compared with the contributions emitted by the fixed particles. In the human body a nominal blood circulation speed of 50 cm/s is reached at present, whereby it can even be several metres per second in the heart. Moreover, the distribution of the speeds in a vessel ranges between zero on the edges of the vessel and nominal speed at the centre of the vessel. Thus, each particle of a vessel contributes to the signal with a phase displacement which can be zero to 50 radians. Knowing that contributions phase displaced by $\pi$ radians mutually oppose one another, the resulting signal is zero, which amounts to taking the mean value of a sinusoidal signal over several periods or cycles. For example, Paul R. Moran in an article in Radiology of RSNA, 1985, 154, pp. 433-441 refers to a measurement of a mean speed equal to 0.6 cm/s and corresponding to a phase displacement of approximately 90°. Beyond this limit, the sensitivity of the machines is too great and the speeds can no longer be measured.

SUMMARY OF THE INVENTION

The object of the invention is to reveal the effect of the speed of the moving parts of a body by modifying the sensitivity of the machines in a particular manner. The sensitivity modification, whilst not modifying in any way the signals emitted by the fixed parts, can have the effect of cancelling out the phase displacement part due to the speed. The moving particles then contribute to the overall signal in the same way as if they were fixed. The process according to the invention also makes is possible to modulate the effect of the speed, instead of cancelling everything out. By carrying out two measurements with different modulation characteristics and by comparing the two measurements, it is possible to eliminate the influence of the fixed parts, so that only that of the moving parts appears. In this comparison, the moving parts appear weighted by the modulation characteristics of the two experiments. In the invention, these characteristics can be calculated and the speed effect can be quantified.

The principle given in the process according to the invention is very general, not being confined to a particular imaging application. It can in particular be realised with resonance spectrometers. Moreover, it is applicable no matter what the radiofrequency excitation procedures adopted are and these can be, e.g. saturation recovery, inversion recovery, double saturation recovery, saturation recovery - inversion recovery, spin echo, etc. Within the scope of image formation, the invention is applicable no matter what the image formation procedure adopted, e.g. no matter whether it is an overhead projection method of the P. C. Lauterbur type, a Fourier transform method of the 3 DFT or 2 DFT type developed by A. Kumar and R. R. Ernst, or its variant known as spin warp (the invention being described with respect to this second method), an image formation method of sensible volumes developed by W. F. Hinshaw, or a fast acquisition method developed by P. Mansfield and known as the echo-planar method, etc. Thus, in all the situations implied by these procedures, the modulation according to the invention is possible, because it consists of modifying the interfering magnetic fields (the field gradients) by adding thereto compensating magnetic fields of a similar configuration and whereof the shape, duration and amplitude characteristics are dependent on said interfering magnetic field.

The present invention specifically relates to a process for the modulation of the speed effect of the moving parts of a body in a density measurement by nuclear magnetic resonance for which the body is exposed to an orienting, constant magnetic field for orienting in a single direction the magnetic spin moments of the body, subjecting said body to a radiofrequency magnetic excitation in the presence of and/or followed by the application of a sequence of an interfering magnetic field and taking a magnetic resonance signal emitted in response by the body, wherein the effect of the speed of the moving parts of the body created by the sequence of the interfering field is modulated by the application prior to the reading, of a sequence of a compensating magnetic field, whereof the integral calculated on its duration is zero and whose history and value are a function of the history and value of the interfering field.

The invention also relates to the performance of the process, wherein it is firstly performed for compensating the speed effect and on a second occasion by modifying one or more of the characteristics of the compensating magnetic field and comparing the measurements obtained in the two performances in order to deduce therefrom the speed of the moving parts in question.

BRIEF SUMMARY OF THE DRAWINGS

The invention is described in greater detail hereinafter relative to an image formation application and with respect to a non-limitative embodiment and the attached drawings, wherein show:

FIG. 1: A machine for performing the process according to the invention.

FIG. 2: Time diagrams of the radiofrequency excitation signals, the interfering magnetic field signals and signals recorded in a special measurement involving image formation of the 2DFT type of a section of a body being examined.

FIGS. 3a and 3b: Time diagrams of phase displacements with the application of sequences of interfering magnetic fields between the contributions emitted by the fixed particles and the moving particles.

FIG. 4: A diagrammatic representation of the response of part of a medium, whereof the particles move as a function of whether said movement in parallel or perpendicular to an imaged sectional plane.

Throughout the drawings the same references designate the same elements.

DESCRIPTION OF THE PREFERRED EMBODIMENT OF THE INVENTION

FIG. 1 shows a machine usable for performing the process according to the invention. It has means symbolized by a coil 1 to subject a body 2 to a constant, strong magnetic field $B_O$. Field $B_O$ is the orienting field. The machine also has generator means 3 and coils 4, connected to the latter for subjecting the thus positioned body to radiofrequency excitation sequences in the presence of interfering field sequences: field gradients oriented in accordance with the three reference axes of the machine X, Y or Z (FIG. 2). At the same time coils 4 represent the radiofrequency coils and the field gradient coils. The machine also has reception means 5 connected to coils 4 for receiving the magnetic resonance signal. In an image formation application, means 6 can make it possible to calculate and store a first image $I_1$ and a second image $I_2$ on a section 7 of body 2. The two images relate to two experimentation series imposed by symbolized controls $C_1$ and $C_2$ of generator means 3. Pointwise comparison takes place in comparison means 8 of the images $I_1$, $I_2$ and a third image $I_3$ is produced. It is possible to display image $I_3$ on a display means 50.

In images $I_1$, $I_2$ or $I_3$, an image or picture point p conventionally represents by its brightness the density of the particles contained in a volume element v corresponding thereto in section 7. The volume element v has numerous particles moving at speeds V having components $V_x$, $V_y$ and $V_z$ on each of the three reference axes of the machine. The invention will make it possible to calculate in volume element v and also in all other volume elements, the means speed or velocity and the number of particles of said moving volume element. Image $I_3$ represents said speed information by comparison between two images $I_1$ and $I_2$, in which the effect of said speed would be modulated in two different ways.

Firstly, brief reference will be made to the theory of image formation by a type 2DFT method, in which there are interfering gradients as in all the other methods. Details will then be given as to why this method is preferable in view of the inhomogeneity problems of the orienting field. Finally, details will be given as to how the compensating fields necessary for modulating the speed effect are calculated.

In order to locate a region in a medium, it is necessary to reference the nature of its emission as a function of the local conditions of magnetic field. These local conditions are imposed in such a way that the emission phase and the frequency are characteristic of the location in space of said region of the medium. For this purpose, on the main field $B_O$ are imposed pulsed magnetic field gradients. These gradients are oriented in directions X, Y and Z to define at all times the volume elements which resonate at known frequencies. For the acquisition of a whole image or picture, the local conditions are imposed in programmed sequences ($C_1$, $C_2$). The latter are stored in a master computer. These sequences define the application times of the gradients, the excitation times of the particles by the radiofrequency field pulses and the reading or acquisition times of the image data.

The image formation method 2DFT makes it possible at present to obtain the best picture quality. In this method, only one sectional plane 7 is excited at once. FIG. 2 shows for this purpose the radiofrequency pulses 10, 11, 12 applied in the presence of a so-called selection field gradient, e.g. oriented along axis Z and respectively represented by pulses 13, 14 and 15. When the selection gradient is oriented along axis Z the section is transversed, i.e. along a plane X, Y. In 2DFT image formation, the different signals acquired are coded in phase. This is obtained by a variable intensity pulse of a so-called phase displacement gradient, whose axis is perpendicular to a so-called reading gradient, whose direction is constant. For example, for a transverse or cross-section, the reading gradient can be on axis X and the phase displacement gradient on axis Y. In FIG. 2, gradient X is 16 and gradient Y is 17. By a double spatial Fourier transform, the image is reconstructed, hence the name of the method. An improvement to this method can also make it possible to simultaneously obtain images of several parallel planes.

The existence of the precoding 17, which takes a certain time, pushes back in time the measurement of the signal emitted by the body. As this signal attenuates very rapidly, it was decided to measure an echo thereof, which is produced at the time of applying the radiofrequency pulses 11 and then 12 by a reflection of the phase dispersion of the contributions made by each of the particles. For this reason these pulses are shown higher in FIG. 2 than pulse 10, because they lead to a flipping of the orientation of the magnetic moments of spins of particles by 180°, whereas pulse 10 only leads to a 90° flip thereof. In order to image a section of the body, spin echo excitation sequences must be performed in the presence of field gradient sequences on a sufficient number of occasions to ensure that the resolution of the expected image is more precise. For each excitation sequence, the phase displacement gradient Y varies by successive steps starting from a certain value and extending to the same value but of the opposite sign. This value is dependent on the shape and duration of the reading gradient 16. Phase displacement gradient makes it possible to rotate each magnetic spin movement by a variable phase, dependent on its ordinate along axis Y and of the value of said gradient. For each image $I_1$ and $I_2$, the gradient Y can successively assume the same number of values and in a preferred manner the definition of the two images is the same.

In order to avoid a parasitic precoding imposed by the end 18 of pulse 13, for the part of said pulse existing after the end of the radiofrequency pulse 10, and by the start 19 of the reading pulse 16, it is known to respectively apply pulses 20, 21 to these axes. The time integral of these pulses is the same, but of opposite sign and they neutralize the parasitic coding effect. The integral is understood in the integral sense in time. Thus, the hatched surfaces 20 and 19 are equal to the dotted surfaces 18 and 21 respectively. Pulses 20 and 21 do not interfere in the section selection, because at the time when they are applied, pulse 10 is no longer present. Pulses 14 and 15 are autoneutralized, because they have respective portions 22, 23 and 24, 25, which are antisymmetrical with respect to the medium of the radiofrequency pulses 11 and 12 for which they reselect the section 7 in body 2.

The 2DFT type image formation method is the most widely used in practice, as a result of its acquisition speed (compared with 3D methods) and its robustness with respect to imperfections of the physical system and in particular with respect to inhomogeneities of the orienting field. This can in particular be appreciated by comparison with overhead projection methods, or with methods not using spin echo. However, this method is also the most intrinsically sensitive to the displacement of the particles. The immunity to the inhomogeneity of the field $B_O$ of the 2DFT method results from the fact that, unlike in overhead projection methods, the frequency coding gradient is of the same direction (reading gradient X) and the same amplitude $G_L$ from one sequence to the next. The inhomogeneity of the field $B_O$ only deforms the isofrequency resonance lines. During the reading of the signal, the inhomogeneity of the field becomes equivalent to a poor linearity of the gradient. Thus, the images are distorted, but do not lead to fuzziness or loss of resolution, which are encountered with overhead projection methods. In the latter, the reading gradient changes orientation for each sequence and consequently it distributes the inhomogeneities of the orienting field throughout the image, so that it leads to fuzziness.

FIGS. 3a and 3b show the phase displacement $\Delta\phi$ resulting in the contribution of the signal emitted by two particles of a same volume element exposed to identical interferences, when one of the particles (continuous line) is stationary, whereas the other particle (broken line) has a speed V. FIG. 3a shows the time diagram of a radiofrequency signal RF having a pulse 26 for producing a spin echo. Along an axis A, a magnetic field gradient has been imposed by taking before and after pulse 26, e.g. a value G during a period $\theta$ on each occasion. At a given place $1_O$, a previously excited, stationary particle vibrates at a frequency $f_O$ at the start of the application of pulse 27. For the duration $\theta$ of said pulse 27, it vibrates at a different frequency. For example, said frequency is higher, so that at the end of pulse 27, as it restarts to vibrate at frequency $f_O$, it can be considered that it has undergone a phase displacement $\phi_1$. During the application of the radiofrequency pulse 26, it can be accepted that everything takes place as if the phase of the signal emitted by said particle was inverted, i.e. $-\phi_1$. During pulse 28, which has exactly the same configuration as pulse 27, the phase displacement phenomenon continues, so that the contribution is phase displaced by $\phi_1$ again. However, this latter phase displacement cancels out the effect of the first after having been reversed or inverted by pulse 26. Consequently, the stationary particle at $1_O$ re-assumes at the end of pulse 28, the phase which it had at the start of pulse 27. It is worth pointing out that the phase displacement $\phi_1$ is proportional on the one hand to the amplitude of gradient G and on other to the time during which each pulse of the gradient is imposed. More generally $\phi$ is proportional to the integral of said gradient during the existence time of its pulse, if said pulse is not exactly rectangular.

The situation is very different for a second particle, which is close in the same volume element of the preceding particle, but which has a speed V. FIG. 3a shows that this particle was successively located in positions $1_O$ to $1_4$ at the start and finish of the first pulse 27, at the time of the radiofrequency pulse 26, and at the start and finish of the second pulse 28 of the gradient. Following the first gradient pulse 27, the resulting phase displacement $\phi_2$ is proportional to the gradient G and to the time $\theta$. However, it is also proportional to the distance $1_1-1_0$ traversed in the interval by the particle. This distance is equal to $V\cdot\theta$. Thus, the time now intervenes to the square: the first phase displacement portion has the configuration of a parabola ($V\cdot G\cdot\theta^2$). From the end of pulse 27 to the start of pulse 28, everything takes place as for the stationary particle: the contribution has a phase $-\phi_2$ at the start of pulse 28. During said pulse 28, the evolution of the phase is also parabolic as for pulse 27. It could be expected that the phase effects would also cancel one another out here. However, between the end of pulse 27 and the start of pulse 28, the moving particle has moved from position $1_1$ to position $1_3$. In the latter position, at the time when pulse 28 appears and due to the existence of the field gradient, the local field conditions are no longer the same as those which prevailed when the particle was between $1_0$ and $1_1$. consequently, at the end of pulse 28, compensation no longer takes place and this moving particle then emits a signal phase displaced by a value $\Delta\phi$, which can be written as follows:

$$\Delta\phi = \gamma \cdot G(\theta) \cdot V \cdot T$$

in which $\gamma$ is the gyromagnetic ratio of the particles in question and $G(\theta)$ represents the gradient in pulses 27 and 28 and in which T is the duration separating the appearance of these two pulses. If $\theta$ is not small, T measures the duration between the centres of these pulses. More generally it is possible to write:

$$\Delta\phi(t) = V \cdot \int_0^t \gamma \cdot G(\tau) \cdot \tau \cdot d\tau$$

in which the phase displacement is now given as a function of time and in which $G(\tau)$ represents all the interferences applied to the particles prior to the measurement of the signal emitted by them at date or datum t. It must merely be borne in mind that the interferences in question are such that:

$$\int_0^t G(\tau)d\tau = 0$$

It is under this condition that, in a manner known in the art (FIG. 2, pulses 18 to 25), that the interfering or parasitic precodings have been compensated. This was obviously not carried out for the variable pulse 17, because the phase displacement caused by it for the overall signal is, between the individual acquisitions, one of the characteristics permitting image formation.

In the absence of a radiofrequency pulse such as 26 producing a spin echo (FIG. 3b), pulses 27 and 28 of the bipolar gradient must be replaced by pulses 29, 30 of opposite signs. In the same way, the phase for the fixed particles evolves up to $\phi_3$ at the end of pulse 29 and evolves in the reverse direction to zero during the reverse pulse 30. The phase displacement $\Delta\phi$ between the contribution of the mobile particles and that of the fixed particles is of the same order as hereinbefore.

In the expression of $\Delta\phi(t)$, $G(\tau)$ consequently represents all the sequences required by the measurement. What characterises the invention is that these sequences are maintained as such, but that their effects on the speed are compensated by the addition of supplementary sequences of so-called compensating field gradients $G'$, such that:

$$\int_0^t (G(\tau)\cdot\tau + G'(\tau)\cdot\tau)d\tau = 0$$

in which G' represents also bipolar gradients, i.e. such that:

$$\int_0^t G'(\tau)d\tau = 0$$

In other words, by acting in this way it is possible to cancel out the multiplying coefficient of the speed V, which appears in the calculation of Δφ(t). Now, no matter what this speed, Δφ(t) is zero and all the contributions are in phase. The mobile particles are taken into account as if they were fixed.

On returning to FIG. 2, it is possible to see on each axis X, Y and Z, the addition of such compensating bipolar gradients in the preferred form of pulse pairs designated 31 and 32, 33 and 34, 35 and 36, 37 and 38, 39 and 40 and 42 and 43. The influence of these compensating pulses is symbolized in the drawing by the presence of small crosses. It is known to impose such pulses in the prior art machines by modifying controls $C_1$ or $C_2$ of the generator means. The time integral of the pulses of each pair is zero. In a preferred manner, because the precoding correction pulse 20 on the selection axis Z is applied between dates $t_1$ and $t_2$ at the end of pulse 13, pulse 31 is applied during the same period and in this case the "new" pulse 20 is stronger. Pulses 35 and 37 are also applied during this period. In a preferred manner, pulses 32, 36 and 38 are applied between the end $t_3$ of pulse 14 and the start $t_4$ of reading pulse 16. Pulses 33, 39 and 42 are applied between the end $t_5$ of pulse 16 and the start $t_6$ of pulse 15. Pulses 34, 40 and 43 are applied between the end $t_7$ of pulse 15 and the start $t_8$ of a pulse 41, which is used for reading a second echo.

From the practical standpoint, the measurement of the emitted signal is carried out between $t'_4$ and $t'_5$ contained in $t_4$ and $t_5$ and also during the duration of pulse 41. Obviously the compensating pulses applied to an axis X, Y or Z have the effect of cancelling out the action of the interfering gradients applied to the same axis. The integral expression implicitly gives the gradients G' and simplifications are possible. Firstly all the terms in G (τ)·τ are known terms (belonging to the sequence 2DFT), so that this also applies to their integral, which can consequently be removed from the expression. In a preferred manner, the shapes of the compensating pulses 31 to 43 will be known and, as far as possible, identical to already used shapes for normal pulses of the interfering sequences. Bearing in mind the date retained for the application of these pulses, a unitary integral of each can be calculated and the expression of G' can be written in another way:

$$\int_0^t G(\tau)\cdot\tau\cdot d\tau + \lambda \int_0^t \Gamma(\tau)\cdot\tau d\tau = 0$$

The first term is known and relates to the interfering gradients. The second term comprises gradient integrals of preferred form Γ and of unity amplitude. It is known to calculate the integral of the second term, because the chosen form Γ is known. Consequently, it is possible to deduce λ therefrom, i.e. the amplitude of the compensating pulses.

In the case of conventional image formation, where at least one gradient is applied during the reading period ($t'_4$, $t'_5$), the implicit equation containing G' cannot be proved for all t. However, it must at least be proved at times $t_{E1}$, $t_{E2}$ forming the centre of the measurement phases and being the dates at which the expected spin echo is strongest. They are such that the time separating the date of the radiofrequency pulse 10 and $T_{E1}$ is double the duration between pulse 10 and pulse 11 and such that the time between date $T_{E1}$ and $T_{E2}$ is equal double the time between $T_{E1}$ and the date of the radiofrequency pulse 12. The justification for these dates is on the one hand intuitive and on the other hand theoretical. The guiding idea in this field is that one wishes to know the state of section 7 not at the time of its excitation (pulse 10), but at time $t_{E1}$ or $t_{E2}$ at which the measurement is performed, i.e. at the centre of the emitted signal.

All the terms of the implicit equation giving G' are known, so that G' can be calculated. FIG. 2 gives a simple approach for this calculation. For axis X, it is known that the pulses 21 and 19 on either side of the radiofrequency pulse 11 mutually neutralize their precoding effects, the integral of the sum of these pulses being zero. However, the integral of the product of these pulses by the duration separating them from the date of reading $t_{E1}$ is not zero, pulse 21 being earlier in time than pulse 19. Thus, everything takes place as if the pulse 21 of given "force" is applied to a longer "lever arm" than pulse 19 of equal force. The effect on the phase of pulse 19 is obviously the reverse of that of pulse 21, because they are located on either side of pulse 11. Consequently their common effect on the phase is analysed as a moment oriented in the direction of the pulse having the greatest lever arm, i.e. pulse 21. It is appropriate to oppose this resultant moment by a pair of pulses 35, 36, whose total integral is zero (leading to no phase displacement on the signal of the fixed parts), but whereof the overall moment is opposed to the overall moment of the two pulses 21 and 19. Thus, as pulse 35 is placed in time at a date preceding pulse 36 with respect to date $t_{E1}$, its effect is preponderant. It is of opposite direction to pulse 21.

In the same way on selection axis Z, of pulses 18, 20 and 22, 23, on each occasion it is pulses 18 and 22 which are preponderant, their lever arm being longer. Thus, pulse 31 must be in the same direction as pulse 20. The case of pulses 37 and 38 is slightly different. Thus, they must oppose the effects of the gradient varying between individual acquisitions. Thus, the amplitudes of pulses 37 and 38 will also vary correspondingly between individual acquisitions (symbolized by the arrows). For the preceding reasons, when pulse 17 is positive, pulse 37 must be negative. In order to be able to reduce the amplitudes of the compensating pulses, every effort is made to give the greatest effectiveness to their moment and attempts are also made to increase the duration separating their application from the date of the reading. They are placed as far upstream as possible of the sequence for the first (31, 35, 37) and as far downstream as possible for the second (32, 36, 38). In conclusion, they are as remote as possible on either side of the radiofrequency pulse 11 and are as remote as possible from one another.

During the first reading at $t_{E1}$, the effects of the speed of the moving parts have been completely compensated. By means of pulses 33, 34, the effects of the second selection pulse 15 is now compensated for. The pivot date for calculating the moments is now $t_{E2}$. On reading axis X, there is also a compensation by two pulses 42, 43 of the effects of the second half 60 of pulse 16 and the first half 61 of pulse 41. The presence of the compensating pulses 39, 40 of axis Y is justified by the fact that pulse 17 is not bipolar. This compensation of its moment at pivot date $t_{E1}$ by pulses 37, 38 does not imply such a compensation at another pivot date, such as $t_{E2}$, even if no supplementary interfering pulse intervenes on said axis in the meantime.

FIG. 4 shows a sensed flow tube 51 in the examined section 7 of body 2. The top of the drawing shows a situation in which tube 51 is coplanar to plane X, Y of the section. In the bottom part of the drawing the situation differs, tube 51 being assumed as perpendicular to the plane X, Y of the section. Volume elements 52 to 55 are shown on either side and are in the form of rectangular parallelipipeds with a substantially square sectional shape. The section is square to the extent that, in image formation, the representative sampling is carried out with the same resolution along axis X and axis Y of the section plane. The major length of the rectangular parallelipiped extends along axis Z, said length being linked with the thickness of section 7. This thickness is an experimental compromise with the fineness of resolution of the sections and the measureable overall signal quantity. The thicker the section, the higher the measureable signal and obviously the less precise the image. In practice, the major dimension is approximately 7 to 15 mm and the square section approximately 1 mm × 1 mm.

A not shown fluid circulates in pipe 51 with a speed diagram 56. The speeds 57 of the particles in the centre are higher than the speeds 58 of the particles located on the edges of the pipe. In the arteries, the speed 57 can be approximately 50 cm/s. When positioned perpendicularly to the section 59 of pipe 51, volume elements 52, 53 necessarily have particles moving at very different speeds. Before the invention, the spread of the speed spectrum is so high that the contribution of volume elements 52, 53 in the overall signal is zero, giving the impression that the tube is hollow. The image of the volume elements 54, 55 can in certain cases be revealing. It is to the extent that said volume elements are located perpendicularly of that part of the section of the pipe where the spectrum of the speeds had a limited spread. This is the case for volume element 55, in which the speeds at the centre of the tube are both high and relatively homogeneous. Their corresponding phase displacement is substantially the same and the mean value is not zero. However, for the volume element 54 positioned straight below the edge of the pipe 51, at the point where the evolution of the speeds is sudden, the restored signal is zero. Thus, the image of the tubes 51 perpendicular to the section plane appeared geometrically smaller than it was in reality. With the invention, the image of the flows is faithfully revealed.

It is possible to modulate the effect of the speed with the process according to the invention. It is merely necessary to not completely cancel out the multiplying coefficient of V in the expression of $\Delta\phi(t)$, in which the compensating gradients are present. The invention proposes effecting a second experiment, in which the compensation is no longer complete and in which, definitively, the measurement is sensitive to this speed effect. A comparison is subsequently made of the results obtained during these two experiments and the speed characteristics are deduced therefrom. In a preferred manner, the modulation is varied along a particular axis, which can be X, Y, Z or even a different axis. In order to vary this modulation, a modification is accomplished on the amplitude λ of the compensating pulses respectively applied to axes X, Y, Z or to a combination thereof.

In the second experiment, it is ensured that the sensitivity to the speed effect is such that for the expected nominal speed to be measured, the maximum phase variation is equal to or less than 1 radian. Under these conditions it can be demonstrated that the speed information is simply obtained by calculating the ratio of the relative variation of the measurements, between individual experiments, to the measurement of the first or second experiment. In other words, if S1 is the result of the first experiment and S2 the result of the second, the mean speed information is represented by $(S_1-S_2)/S_1$. Beyond this sensitivity on the one hand the proposed calculation is no longer applicable to obtain speed information and on the other hand there is a risk of the sensitivity being so great that the difficulty solved by the invention might be encountered again. It is a calculation of this type which is performed by comparison means 8. It is performed picture element by picture element. Between the individual experiments, the sensitivity passed from zero to a certain value calculatable by the integral of $G(T)\cdot T$ and $G'(T)\cdot T$, so that it is possible to quantify the measured speed.

According to a preferred variant, the invention is realized in an excitation method with gradient echo. Such a method is preferred as compared with the hitherto described spin echo method. Thus, in a spin echo method, the radiofrequency pulse making the magnetic moments of the particles flip by 180° has a slightly over estimated redundant frequency band (of shorter duration) for rephasing the contributions of all the particles which had entered into resonance due to the 90° pulse. This redundancy can in itself lead to the parasitic excitation of particles close to edge 7. However, now with the compensation, it is possible to code these adjacent particles (by pulse 38 or 40). Thus, the parasitic signal produced by them can vary from one sequence to the next. Under these conditions, it would no longer be possible to extract the useful signal. Thus, if it remains constant, it is possible to eliminate it by effecting a double acquisition. If it is not eliminated, its presence can be very distrubing. In a sequence with gradiant echo (FIG. 2), the radio frequency pulse 11 (and 12) is eliminated. The second selection pulse 14 no longer has to exist. The equilibrating pulse 21 of the reading pulse 16 is of the opposite sense and pulse 17 is unchanged. The gradiant echo is brought about by the equality of areas 21 (reversed) and 19. Under these conditions, the disturbing gradients all have shapes comparable to those of FIG. 3b. However, they are compensated in accordance with the same principle as for those of FIG. 3a. For the compensation of the phase coding gradient, the compensating pulses 37 and 38 are maintained as they are. As there is no longer a spin echo, there can no longer be a parasitic signal which it is impossible to eliminate.

What is claimed is:

1. A process for the modulation of the speed effect of the moving parts of a body in a density measurement by nuclear magnetic resonance, comprising the steps of;

exposing said body to an orienting, constant magnetic field for orienting in a single direction the magnetic spin moments of the body;

subjecting said body to a radio frequency magnetic excitation in the presence of and/or followed by the application of a sequence of an interfering magnetic field; and detecting a magnetic resonance signal emitted in response by the body;

wherein the effect of the speed of the moving parts of the body created by the sequence of the interfering field is modulated by the application, prior to the step of detecting, of a sequence of a compensating magnetic field, an integral of said compensating magnetic field calculated on its duration being zero, and whose history and value are a function of the history and value of the interfering field wherein the sequence of the interfering magnetic field has magnetic field pulses along three orthogonal axes and wherein the sequence of the compensating magnetic field has magnetic field pulses along these three same axes, in order to individually modify the effects of the speed of the moving parts of the body along said three axes wherein the compensating magnetic field pulses are determined a priori by position and duration $\Gamma$; and, wherein amplitude $\lambda$ is evaluated to obtain the modulation.

2. A process for the modulation of the speed effect of the moving parts of a body in a density measurement by nuclear magnetic resonance, comprising the steps of:

exposing said body to an orienting, constant magnetic field for orienting in a single direction the magnetic spin moments of the body;

subjecting said body to a radio frequency magnetic excitation in the presence of and/or followed by the application of a sequence of an interfering magnetic field; and, detecting a magentic resonance signal emitted in response by the body;

wherein the effect of the speed of the moving parts of the body created by the sequence of the interfering field is modulated by the application, prior to the step of detecting, of a sequence of a compensating magnetic field, an integral of said compensating magnetic field, calculated on its duration being zero, and whose history and value are a function of the history and value of the interfering field;

wherein the radio frequency magnetic excitation has a radio frequency pulse for flipping by 90° the orientation of the magnetic moments of the spins, followed by a gradient echo pulse and wherein the echo of the signal emitted in response after being reflected by the gradient echo pulse is acquired as the magnetic resonance signal.

3. A process for the modulation of the speed effect of the moving parts of a body in a sensitivity measurement by nuclear magnetic resonance, comprising the steps of;

exposing said body to an orienting, constant magnetic field for orienting in a single direction the magnetic spin moments of the body;

subjecting said body to a radio frequency magnetic excitation in the presence of and/or followed by the application of a sequence of an interfering magnetic field; and detecting a magnetic resonance signal emitted in response by the body;

wherein the effect of the speed of the moving parts of the body created by the sequence of the interfering field is modulated by the application, prior to the step of detecting, of a sequence of a compensating magnetic field, an integral of said compensating magnetic field calculated on its duration being zero, and whose history and value are a function of the history and value of the interfering field;

wherein the process is performed on occasions for each of which pluralities of sequences are achieved in order to produce images of theparts of the body;

wherein the process is performed on a first occasion to compensate the effect of the speed and on a second occasion by modifying one or more of the characteristics of the compensating magnetic field but by not nullifying these compensating magnetic field; and, wherein the measurements obtained are compared in the two performances in order to deduce therefrom an image of the speed of the moving parts in questions.

4. A process according to one of claims 1, 2 or 3, wherein the sequence of the compensating magnetic fields involves bipolar pairs of pulses.

5. A process according to one of claim 1 or 3, wherein the sequence of compensating magnetic fields involves pairs of pulses, each pulse of a pair being of the same value, shape, duration a nd sign as the other pulse of the pair, said pulses being respectively before and after a second radio frequency pulse.

6. A process according to one of the claims 1 or 2, wherein the integral of the product of the value of the interfering field pulses by the duration separating them from the reading of the emitted signal is compensated by the integral of a same product, obtained with the compensating field pulses.

7. A process according to claim 4, wherein the pulses of the pulse pairs involve pulses which are as far spaced from one another as possible.

8. A process according to one of claims 1 or 3, wherein the radio frequency magnetic excitation involves a first radio frequency pulse for flipping by 90° the orientation of the magnetic moments of the spins, followed by at least one second radio frequency magnetic pulse for flipping by 180° the orientation of the magnet moments of the spins and wherein the echo of the signal emitted in response is taken as the magnetic resonance signal after it has been reflected by the second radio frequency pulse.

9. A process according to any one of the claims 1, 2 or 3 wherein the measurement involves the production of the image of a volume, whereof the position and dimensions are determined by sequences of the interfering magnetic field.

10. A process according to any one of the claims 1, 2 or 3 wherein the measurement involves the production of an image of a selection of the body, whose position therein is determined by sequences of the interfering magnetic field.

11. A process according to claim 9, wherein the production of the image is performed in accordance with a three dimensional inverse Fourier transform type process (3DFT).

12. A process according to claim 11, wherein the image is produced in accordance with a bidimensional inverse Fourier transform type process (2DFT).

13. A performance according to claim 3, wherein the modification relates to the characteristics of the compensating magnetic field relative to one axis in order to deduce therfrom the velocity component of the moving parts along said axis.

14. A performance according to claims 3 or 13 wherein the modification is such that the phase displacement corresponding to the signal emitted by the moving parts moving at a nominal speed is approximately 1 radian.

* * * * *